US012159397B2

(12) United States Patent
Perrot et al.

(10) Patent No.: US 12,159,397 B2
(45) Date of Patent: Dec. 3, 2024

(54) METHOD AND SYSTEM FOR DETERMINING A CHARACTERISTIC OF A KERATINOUS SURFACE AND METHOD AND SYSTEM FOR TREATING SAID KERATINOUS SURFACE

(71) Applicant: L'OREAL, Paris (FR)

(72) Inventors: Matthieu Perrot, Clichy (FR);
Emmanuel Malherbe, Clichy (FR);
Thierry Wasserman, Clichy (FR);
John Charbit, Clichy (FR);
Panagiotis-alexandros Bokaris, Clichy (FR)

(73) Assignee: L'Oreal, Paris (FR)

( * ) Notice: Subject to any disclaimer, the term of this patent is extended or adjusted under 35 U.S.C. 154(b) by 633 days.

(21) Appl. No.: 17/277,166

(22) PCT Filed: Jul. 15, 2019

(86) PCT No.: PCT/EP2019/069047
§ 371 (c)(1),
(2) Date: Mar. 17, 2021

(87) PCT Pub. No.: WO2020/057803
PCT Pub. Date: Mar. 26, 2020

(65) Prior Publication Data
US 2022/0005189 A1    Jan. 6, 2022

(30) Foreign Application Priority Data
Sep. 20, 2018 (EP) .................................. 18195776

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0075* (2013.01); *A61B 5/448* (2013.01);
(Continued)

(58) Field of Classification Search
CPC ........... G06T 7/0012; G06T 7/10; G06T 7/90; A61B 5/0075; A61B 5/448
See application file for complete search history.

(56) References Cited

U.S. PATENT DOCUMENTS

| 11,680,063 B2* | 6/2023 | Polykovskiy ........ G06V 10/764 |
| | | 702/19 |
| 2007/0058858 A1 | 3/2007 | Harville et al. |

(Continued)

FOREIGN PATENT DOCUMENTS

| JP | 2012516760 A | 7/2012 |
| JP | 2014128487 A | 7/2014 |

(Continued)

OTHER PUBLICATIONS

International Search Report issued on Sep. 10, 2019 in PCT/EP2019/069047 filed on Jul. 15, 2019.
(Continued)

*Primary Examiner* — Kevin Ky
(74) *Attorney, Agent, or Firm* — CHRISTENSEN O'CONNOR JOHNSON KINDNESS PLLC

(57) ABSTRACT

The present application is directed to a method and system for determining at least one physical and/or chemical characteristic of a keratinous surface of a user, the method comprising the steps of: —receiving data corresponding to at least one image of the keratinous surface, —processing the image by applying at least one machine learning model to said image, —returning at least one numerical value corresponding to a grade of the characteristic of the keratinous surface to be determined.

15 Claims, 2 Drawing Sheets

(51) Int. Cl.
  *G06T 7/10* (2017.01)
  *G06T 7/90* (2017.01)
(52) U.S. Cl.
  CPC ............... *G06T 7/10* (2017.01); *G06T 7/90*
    (2017.01); *G06T 2207/10048* (2013.01); *G06T*
    *2207/20081* (2013.01); *G06T 2207/20084*
    (2013.01); *G06T 2207/30088* (2013.01); *G06T*
    *2207/30201* (2013.01)

(56) References Cited

U.S. PATENT DOCUMENTS

| | | | |
|---|---|---|---|
| 2013/0278746 A1* | 10/2013 | Pulyassary | G01N 21/31 348/81 |
| 2016/0148080 A1* | 5/2016 | Yoo | G06V 40/171 382/118 |
| 2017/0255878 A1* | 9/2017 | Fu | G06N 20/00 |
| 2017/0270593 A1 | 9/2017 | Sherman et al. | |
| 2018/0014777 A1 | 1/2018 | Amir et al. | |
| 2018/0260871 A1* | 9/2018 | Harvill | G06F 3/04847 |
| 2018/0303397 A1* | 10/2018 | Krupat | G16H 50/20 |
| 2019/0170904 A1* | 6/2019 | Topolancik | B82Y 20/00 |
| 2020/0060603 A1* | 2/2020 | Bower | A61B 5/167 |
| 2020/0193503 A1* | 6/2020 | Mathiaszyk | G06Q 30/0623 |
| 2020/0221994 A1* | 7/2020 | Kumpan-Bahrami | A61B 5/0002 |
| 2020/0375466 A1* | 12/2020 | Ras | A61B 5/0077 |
| 2021/0076807 A1* | 3/2021 | Pack | A45D 44/005 |
| 2022/0005189 A1* | 1/2022 | Perrot | G06T 7/0012 |
| 2023/0210245 A1* | 7/2023 | Lee | A45D 34/04 132/200 |

FOREIGN PATENT DOCUMENTS

| | | |
|---|---|---|
| JP | 2017519193 A | 7/2017 |
| JP | 2018068601 A | 5/2018 |

OTHER PUBLICATIONS

Cosco, "Cover Girl Launches AI-Driven Customization App—WWD", Feb. 6, 2017, XP055533554, Retrieved from the Internet: URL:https://wwd.com/beauty-industry-news/color-cosmetics/cover-girl-launches-ai-driven-customization-app-10777590/ [retrieved on Dec. 12, 2018], 4 pages.

Hameed et al., "A comprehensive survey on image-based computer aided diagnosis systems for skin cancer", 10th International Conference on Software, Knowledge, Information Management & Applications (SKIMA), IEEE, 2016, pp. 205-214, XP033090777, no date available.

Anonymous, "Henkel Beauty Care Presseinformation, CES 2018: Henkel Beauty Care stellt Friseursalon der Zukunft vor", Jan. 3, 2018, XP055533533, Retrieved from the Internet: URL:https://www.henkel.de/blob/816646/19a560596ce96c516960e4b3716b4dbc/data/2018-01-03-presseinformation-henkel-beauty-care-salonlab.pdf [retrieved on Dec. 12, 2018], 4 pages.

Search Report and Written Opinion issued in corresponding European Application No. PCT/EP2019/069047, filed Jul. 15, 2019, 8 pages.

Office Action issued in corresponding Chinese Application No. 201980061174.X, filed Jul. 15, 2019, 14 pages.

Office Action issued in corresponding Korean Application No. 10-2021-7007390, filed Jul. 15, 2019, 5 pages.

Office Action issued in corresponding Japanese Application No. 2021-538896, filed Jul. 15, 2019, 8 pages.

Cosco, Amanda, "Cover Girl Launches AI-Driven Customization App", WWD, Feb. 6, 2017, Retrieved from the Internet: URL:https://wwd.com/beauty-industry-news/color-cosmetics/cover-girl-launches-ai-driven-customization-app-10777590/, 4 pages.

Hameed, Nazia, et al., "A comprehensive survey on image-based computer aided diagnosis systems for skin cancer", Dec. 2016 10th International Conference on Software, Knowledge, Information Management & Applications (SKIMA), 2016, pp. 205-214.

\* cited by examiner

[Fig. 1]
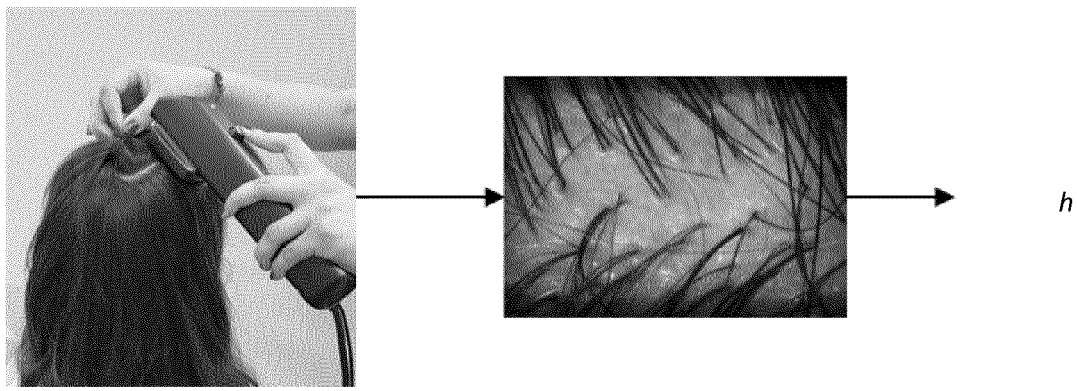
[Fig 2]
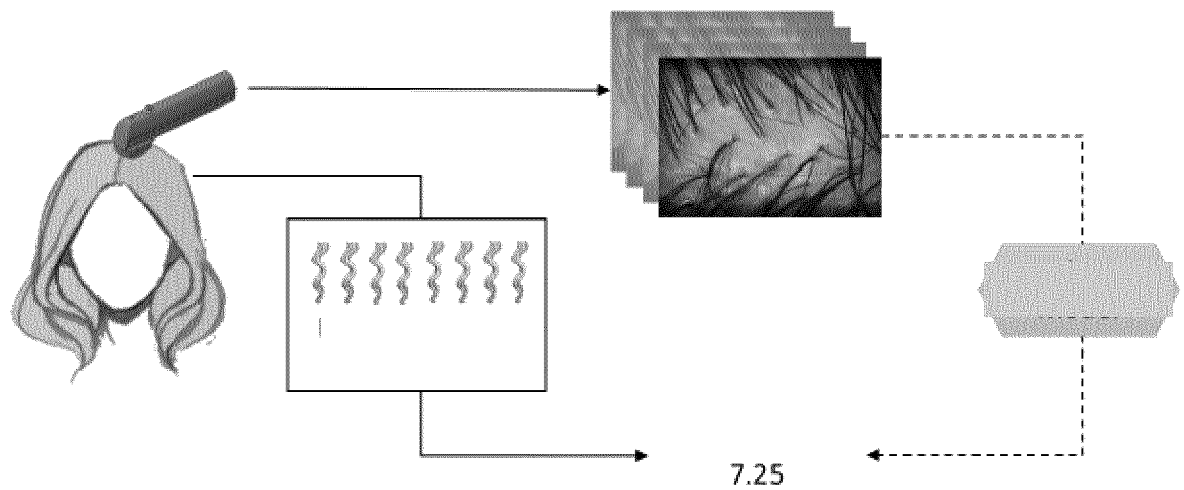

[Fig. 3]
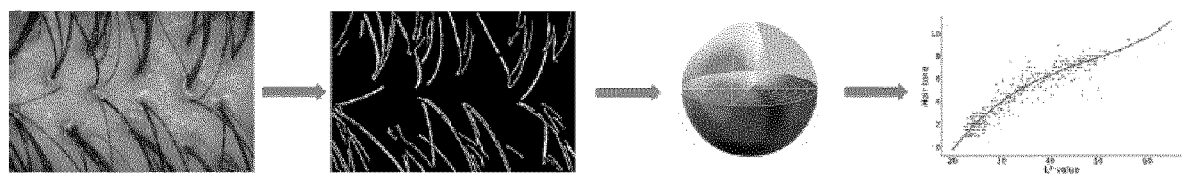
[Fig. 4]
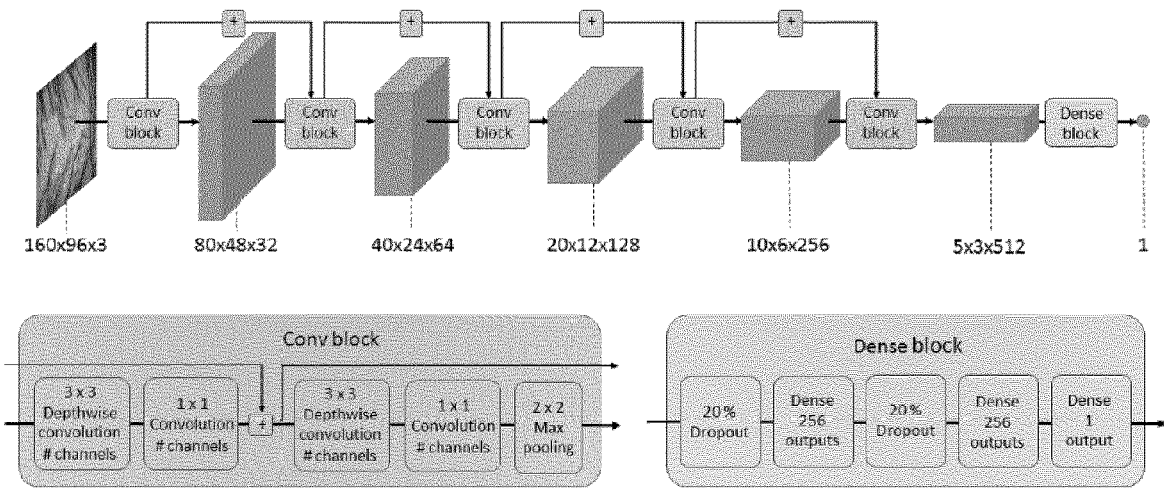

METHOD AND SYSTEM FOR DETERMINING A CHARACTERISTIC OF A KERATINOUS SURFACE AND METHOD AND SYSTEM FOR TREATING SAID KERATINOUS SURFACE

The present invention relates to a method and system for determining at least one characteristic of a keratinous surface and to a method and system for treating said keratinous surface.

The method is particularly directed to the evaluation and treatment of human hairs, and more particularly, to a method and system for bleaching or dyeing hairs such as disclosed in document WO2004002300A2 and U.S. Pat. No. 9,316,580B2 for example.

The health and beauty industry leverages advances in technology to improve the consumer experience with their products and services. There is a deep trend to offer products that are tailored to the user's needs and fit its specific traits. This trend is generally called "personalization".

"Personalization" can pertain to any body part but is of particular interest for exposed body parts such as the face (makeup or care products, in particular foundation) and scalp/hairs (care or dyeing products for example).

It is known to offer and recommend foundation makeup products based on at least one property of the user's skin (such as "Le Teint Particulier"® by LANCÔME®). It is also known to offer and recommend hair products based on some properties of the hairs.

"Personalization" goes beyond the mere offering of a more or less broad range of products corresponding each to a dedicated category of users, the challenge often being to be able to recommend the most appropriate product to the concerned user depending on its personal traits.

In a general way, "personalization" comprises a first diagnostic step aiming at obtaining data that are specific to said user, the data being then used to determine an appropriate subsequent treatment and/or product(s) to be applied to the user concerned body part.

Until recently, some or all the steps were often used to be performed manually or visually by an expert such as a hairdresser or a beauty adviser. It is for example known to address the user with a specific questionnaire, the answers of which are used to determine the allegedly most suitable product (e.g US-A1-2014/0216492). Of course such a method is highly variable and subjective and there is a general need to improve both the relevancy and the reliability of the product recommendation.

In order to improve the relevancy and reliability of the product recommendation, some or all the steps may be performed using tools and devices and even be automated.

For example, obtaining data from the user's concerned body part can be done through measurement using an appropriate measurement device (called a "reader") for obtaining one or more specific features that are looked after for determining the appropriate treatment or product. An example of such a device is the CAPSURE reader marketed by X-RITE and able to return a color data code of the skin of a user.

The collected data may then be fed (possibly with other additional data) to a computing unit that will help determining the most suitable product according to various set of rules.

The subsequent treatment or product determined according to the collected data may be a ready-made product chosen from a catalogue or in a database (such as in documents U.S. Pat. No. 5,478,238 or U.S. Pat. No. 9,519,927 disclosing methods for finding a matching foundation products) or a personalized product, the composition of which has been determined based on the previously obtained data.

The recommended product may then be bought or ordered by the user. In case of a personalized product (or custom-made product), said personalized product may be then manufactured on site, directly in the shop or in the beauty/hair salon by a device able to mix components according to the personalized composition and dispense said composition. The personalized product may also be ordered by the user for a later delivery.

As a full example of such a system, the above mentioned document U.S. Pat. No. 9,316,580B2 discloses a method of performing a customized treatment of keratinous fibers comprising a diagnostic step using an optical reader configured to acquire a spectrum of the hairs, said spectrum being used to compute a subsequent hair treatment composition, the appropriate composition being then made and dispensed by a corresponding device. One may also refer to document WO2011024160A1.

As mentioned above, obtaining reliable, objective and relevant data from the user may be particularly challenging. This is especially the case for hairs or scalp due to their specific texture and environment.

Depending on the desired information that are looked for, different techniques may be used:

Document KR-A1-101456942 discloses a hair and scalp condition diagnostic device comprising a sensor unit to diagnose a user's hair or scalp condition objectively by comparing previously stored hair or scalp samples based on diagnosis signals diagnosed by a hair or scalp condition. In particular, the device may comprise an image sensor for acquiring images of an area of the scalp. The acquired images may be then processed through an image analysis module using for example light intensity recognition, color recognition or contrast analysis in order to determine some properties of the hairs such as number of hairs, diameter, etc. Although this document states that the hair and the scalp are strong in contrast and can thus be clearly distinguished from each other in the image, this is actually often not the case since hairs are at least partially translucent depending on the level of melanin they contain. This is particularly true for thin hairs, white and blond hairs, which are the most difficult to identify and count.

Document WO2017207455 filed in the name of the present applicant also proposes a method for analyzing a condition of the scalp and/or hairs comprising the step of taking pictures under different lighting conditions (white light and UV-Blue light), in order to improve detection of the hairs and better reveal light and white hairs. The images are then processed namely through contrast analysis in a complementary way.

Document US2012253203 discloses a method for imaging a skin surface presenting hairs, such as an area of the scalp in order to determine a skin and hair growth condition. The method comprising taking pictures of the concerned surface under different viewing angles, said pictures being then potentially processed by computer analysis in order to determine properties such as number of hairs protruding from the skin surface, thickness of hairs, diameter or cross sectional shape of hairs, length of hairs protruding from the surface.

Document US2009036800 pertains to a hair densitometer. The densitometer works by taking magnified pictures of an area of the scalp. Hairs visible in the image may be counted and measured by a technician or by any suitable automated system.

Depending on the specific feature to be determined, specific algorithms must be developed to process the images. Such algorithms may require high calculation power and lack versatility as they are dedicated to work on a specific feature. In the specific area of hair property measurement, the very nature of hairs, makes it particularly difficult to design algorithms.

In addition, in the specific area of hair dyeing or bleaching, reliable and true diagnostic of the original hair color is paramount since it will have a strong impact on the final color to be obtained. Usually, this is done visually by an expert, such as the user's hair dresser, according to his expertise and the help of scales showing different hair tones and hair colors.

Early 2003, the company COLORIGHT, now part of L'OREAL's group proposed a system for determining and preparing a hair dye composition based on the color of the user's hairs. Color data is classically obtained by using a spectrophotometer, the spectrum of which is used to compute the appropriate hair dye composition and predict the final dying result. For additional information about COLORIGHT's applications, one may refer to previously cited document WO2004002300 and subsequent applications. Later previously cited patent U.S. Pat. No. 9,316,580B2 is also of particular relevance for a description of the global system.

There exist several documents directed to the measurement of the user's hair color.

One may refer to document U.S. Pat. No. 6,067,504 disclosing a method for correctly identifying hair color using a colorimeter. The method further uses the Hunter L, a, b values of hair and use these to propose an appropriate coloring agent that can achieve the desired hair tone from a predefined database.

A particular issue with using a spectrophotometer for measuring hair color is that it takes a spectrum of the whole measurement area, said area including skin of the scalp and hairs. Spectrophotometers are capable of measuring an object color with high accuracy but they are averaging its value over the whole measurement area, usually on the order of 1 cm$^2$. Thus, the color actually obtained from the spectrum does not exactly correspond to the true color of the user's hairs and may require correction.

In the specific context of hair color measurement, spectrophotometer cannot be used near the scalp for root measurements, as they would average the whole area, mixing hair and scalp values and being highly dependent on the exact area being measured.

Furthermore, a spectrophotometer or colorimeter is dedicated to color measurement and obtaining additional relevant data such as the density of hairs, etc, is not possible or requires additional sensors or additional dedicated device.

In order to improve reliability of the measurement, document U.S. Pat. No. 7,508,508 discloses the combined use of a spectral analysis unit and an image unit, said image unit being used to display the image of the measured area thus allowing the operator to precisely control the measured area and perform a complementary visual assessment. Such a solution is still complex and is not fully satisfactory.

One may also refer to document U.S. Pat. No. 7,151,851 describing a cosmetic color analysis system that analyzes the color of a three dimensional object, such as hair, through acquisition by a camera sensor and produces a cosmetic color determination by relative weighing of multiple cosmetic colors. However, the system does not take the scalp and hair environment into account.

In another approach, document U.S. Pat. No. 8,428,382 proposes a method and an apparatus for displaying images of hair regions in order to evaluate the hair styling using image processing.

However, despite the various trials, a functional device that succeeds in transforming hair diagnosis remains a challenging topic.

There is a need to further develop the system and allow for versatile, reliable and objective collection of scalp and hair data. In addition, hair color and hair density are not the only relevant parameters and one may wish to collect other parameters specific to the user.

To this end, there is a need for an improved method for diagnosing a condition of the skin, scalp and/or hairs, in order to obtain reliable data specific to a user that may be then used with a personalized product recommendation system or in a personalized dispensing or composition manufacturing system.

The present application proposes a solution to at least part of the above mentioned limitations and pertains to a method for determining at least one physical and/or chemical characteristic of a keratinous surface of a user, the method comprising the steps of:
   receiving data corresponding to at least one image of the keratinous surface, (input image)
   processing the image by applying at least one machine learning model to said image,
   returning at least one numerical value corresponding to a grade of the characteristic of the keratinous surface to be determined.

It has indeed been surprisingly found that, after having been trained with a proper training set, machine learning models applied to images of the user's skin could give good results in evaluating and grading a physical and/or chemical property of the keratinous surface to be measured.

While remaining simple to use and implement since it is image based (machine vision) and does not require specific sensor, it has also been found that analyzing images by using machine learning model could help assessing properties that are either significantly hard or impossible to assess by the naked eye, even an expert eye.

By returning or outputting a numerical value (different from a label predicted by a classification model), the proposed method allows for a quantitative determination of the desired characteristics. The quantitative value may then be used as an input data in further calculations and transformations. This goes beyond mere classification where a class or category is returned even if the label of the category may use numbers.

More precisely, the returned numerical value is a continuous output variable which is a real-value such as an integer or floating-point value. These are often quantities such as amounts and sizes.

The machine learning model is a regression model. Alternatively, the machine learning model is a classification model where the labels have an ordered relationship (discretization model), said labels being ordered to a continuous range corresponding to the physical/chemical characteristic to estimate.

It is important to note that while a classification model may predict a continuous value, said value is in the form of a probability for a class label. A regression model may predict a discrete value, but said discrete value is in the form of an integer quantity.

Preferably the image is a high resolution image.

Preferably, the image is a macro image of the keratinous surface. As commonly understood a macro image is an image shot at a magnification ratio of 1:1 or higher. Preferably, each pixel has a maximum size of 10 µm so as to have several pixels along a diameter of a hair strand.

The image data can be obtained through a known image sensor such as a CMOS or CCD image sensor. In addition, the image is advantageously parallax-free.

Advantageously, the method comprises a pre-processing image segmentation step, the machine learning model being applied to at least one identified segment. Image segmentation aims at extracting significant objects associated with the characteristic to determine. Image segmentation is the process of partitioning the digital image into multiple segments or sets of pixels in order to simplify and/or change the representation of an image into something that is more meaningful and easier to analyze. Image segmentation is typically used to locate objects and boundaries (lines, curves, etc.) in images. Such a pre-processing step will enhance the prediction made by the machine learning model by highlighting specific objects in the image data. For example, an image of the scalp can be segmented in order to identify pixels that are highly likely to be hairs. The machine learning model can then be applied to those specific segments for better prediction.

According to a first embodiment, the segmentation step is performed by contrast analysis. According to a second embodiment, the segmentation step is performed by applying a machine learning model to the image, namely a classification model.

Other pre-processing steps may be performed on the image data such as color calibration and correction.

Preferably, the image is an RGB image. Alternately, the image may be a CMYK image or encoded in another color space. Alternately, the image is a multispectral image comprising at least one spectral band chosen among the visible spectral band 380 nm to 700 nm, the UV band 300 to 380 (or even 200 to 380 nm for Near UV band) nm and the IR band 700 to 1500 nm. The image may also be an infrared image.

In a specific embodiment, the method is repeated in order to determine a second characteristic of the keratinous surface, the method being preferably repeated using the same image data. Indeed, by simply loading an appropriate model, it is simple to process the same image in order to obtain an estimate value for another characteristic. Preferably, the method uses data of a single image, even when different machine learning models are applied, the models being applied to the same single image.

Advantageously, the method comprises a subsequent step of recommending a cosmetic product based on at least some of the real-valued characteristic(s). As it is known, the product may be selected in a database depending on its listed properties.

According to the present application, a «cosmetic product» or a «cosmetic composition» is understood to mean a product as defined in European Council and Parliament Regulation 1223/2009 of Nov. 30, 2009, pertaining to cosmetic products.

In a specific embodiment, the method comprises a subsequent step of determining a recommended cosmetic product composition based on at least some of the real-valued characteristic(s).

Of course additional parameters and characteristics obtained through different ways (measurement, questionnaire, image analysis) may be taken into consideration in combination when determining the recommended product and composition.

Advantageously, the method comprises the subsequent step of making and dispensing a cosmetic product according to the recommended composition. In particular, the method comprises the step of mixing at least some of the components in a mixing unit. In the particular case of hair dye, the method comprises the step of dispensing at least one hair dye coloring agent (preferably in a solid form as a bead or tablet) into a hair dye oxidation base agent (preferably in the form of a liquid or cream).

Preferably, the keratinous surface pictured in the image is an area of the skin of a user. In a first embodiment, the area of the skin pictured in the image is an area of the face of the user, preferably an area of a cheek and/or forehead of the user. Alternately, the area of the skin pictured in the image is an area of the scalp of the user. In a most preferred embodiment, the area of the skin pictured in the image comprises hairs.

Advantageously, the area pictured in the image is a hair-root region of the user. The roots of hair (i.e. the first centimeter away from the scalp) present us with clean hair fiber portions that have not been subjected to color change due to hair dyeing or environmental conditions. Therefore, they are a measure of a person's baseline hair characteristics.

According to the present application, the characteristic to be determined is chosen among hair tone, hair diameter, hair density, percentage of white hair, length color, root color, hair shine, scalp dryness, dandruff degree, hair colorimetry, hair spectrum, Eulamin level, Pheomelanin level, level of artificial dyes, moisture, level of cysteic acid, damage level, lift level, the machine learning model having been trained accordingly to evaluate said characteristics.

Preferably, the machine learning model is a pre-trained Convolutional Neural Network.

In a first specific embodiment, the method is directed to the determination of natural hair tone of a user, the method comprising the step of:
  receiving data corresponding to an image of a scalp surface of the user, said image comprising hairs, preferably parted along a median line of the image,
  segment the image in order to extract sets of pixels that to correspond to probable hairs,
  transform color space values of the segmented hair pixels into CIELAB color space,
  return a real-valued hair tone estimate based on median lightness value of the segmented hair pixels.

In a second specific embodiment, the method is directed to the determination of natural hair tone of a user, the method comprising the step of:
  receiving data corresponding to an image of a scalp surface of the user, said image comprising hairs, preferably parted along a median line of the image,
  return a real-valued hair tone estimate by applying a pre-trained Convolutional Neural Network. Although possible, this method does not need a segmentation step as it appeared that a properly pre-trained CNN would not require segmentation in order to give good results.

The present application also pertains to one or more non-transitory computer storage media storing computer-useable instructions that, when used by a computing device, cause the computing device to perform a method according to the invention.

The present application is also directed to a system for implementing the method according to the invention and more precisely to a system for determining at least one physical and/or chemical characteristic of a keratinous surface of a user, said system comprising an image sensor configured for acquiring an image of the keratinous surface and to transmit the image data to a processor, said processor being configured to process the image data according to a method of the invention.

As mentioned above, the image sensor may be a sensor known in the art such as a CCD sensor or a CMOS sensor. Depending on the desired image, the sensor may also be a multispectral sensor and/or use filters such as an infrared filter in order to obtain an infrared image.

Advantageously, the system is at least partially integrated into a portable camera device.

Preferably, the system comprises a camera device including the image sensor, said camera device being configured to transmit the image data wirelessly to a distant processing device.

Alternatively, the camera device may also include the processing unit and directly output the returned property value. This way the camera device forms an autonomous diagnosis unit that can be easily handheld and used as a standalone device.

The present application is also directed to a system for making a personalized cosmetic product, in particular a hair care or hair coloration product, comprising a characteristic determination system (preferably a unit, namely handheld) according to the invention and a dispensing unit configured to deliver a cosmetic product according to characteristics obtained from the characteristic determination system. Advantageously, the characteristic determination system can transmit the real-value data wirelessly to the dispensing unit. More precisely, the characteristic determination unit will forward the real-valued characteristic as an input to a computing unit (recommending) that will determine a suitable output product or composition. The recommending unit may then send input instructions to a mixing and delivery unit in order to provide the user with the recommended product or composition.

The subject of the present application will be better understood in view of the following detailed description made in reference with the attached drawings in which:

FIG. 1 generally illustrates the various sequenced steps for determining a user's natural hair tone according to the present invention.

FIG. 2 generally illustrates the training process involved in obtaining the machine learning models to be applied.

FIG. 3 shows the step pipeline for use of a colorimetric model.

FIG. 4 illustrates the various layers applied to the acquired image of the scalp.

Although the present application is particularly relevant to scalp and hair diagnostic and hair property measurement, it is not limited to such keratinous surface and may find application in more general skin surface characterization and measurement.

As mentioned above, a sector that faces many challenges in this digital era is hair care and hair coloration. Due to the complex nature of hair and the process of hair dyeing, accurate hair diagnostics is crucial in order to provide the clients with personalized hair care and coloration products.

Hair related characteristics being the most challenging to obtain in a reliable way, the following description is illustrated by hair measurements. However, as mentioned, the present method is not limited to hair measurement and may find other skin applications.

Currently at hair salons, the first necessary step before applying any hair coloring product or recommending a hair treatment is hair diagnosis. Among the important features that the hairdresser needs to estimate are the hair tone, white hair percentage, hair diameter and density.

The root of the hair is commonly the only region where we have access to hair that has not been altered by external factors, such as natural/artificial colorants. It is a region where we can measure natural hair color and white hair percentage as well as hair density.

The roots of hair (i.e. the first centimeter away from the scalp) present us with clean hair fiber portions that have not been subjected to color change due to hair dyeing or environmental conditions. Therefore, they are a measure of a person's baseline hair characteristics.

Images acquired in the roots region show not only hairs but also the scalp that can vary highly in color, oiliness, and dandruff content. In addition, the hair fibres themselves, particularly at the root portion, are translucent, resulting in color dependence on the scalp background, and have a certain natural variability both in color and thickness. This diagnosis is currently made manually by hairdressers, and despite their expertise and training they are not always capable of making accurate estimations of all of these features, especially in the non-standard lighting conditions of hair salons.

Establishing accurate hair diagnostics at roots is a significant challenge with dramatic impact on hair coloration, beauty personalization and clinical evaluation.

The method according to the present application will be illustrated in details for hair tone measurement (especially natural hair tone measurement), however it may be used more generally for determining other physical or chemical properties depending on the property for which the model has been trained.

Natural hair tone is the visual attribute of the hair lightness/darkness and is related to the hair melanin concentration. As such, it is bound by the color space of hair colors existing in nature. It is traditionally measured using a logarithmic scale starting at 1, for very dark hair, to 10 for very light blond hair.

Since the hair tone is separated in 10 categories, one could address this problem as a classification problem. However, color experts have assessed tones with a precision of ¼ hair tone, so considering 1 to 10 classes would lose this accuracy in class labels. The problem has consequently been addressed as a regression problem, which assumes an order and continuity between the values of hair tone. Consequently, the method estimates and returns a real-valued hair tone.

Regarding the present method for valuing a hair property, important point is that hair tone scale is a perceptually linear scale notation that is appropriate to use with the present method returning a numerical value (prediction) and not a class per se (classification).

According to the present application, determining a user's natural hair tone comprises the following steps, the general sequence of which is shown on FIG. 1.

First, an image I of the user's scalp 10 at hair roots 11 is taken using a camera device 20 forming a diagnosis unit. The camera device 20 is preferably handheld. The image I corresponds to an object (scalp) area of about 12×17 mm. The image I is acquired by a 2000×1200 RGB CMOS sensor, but other kind of high resolution sensors may be used.

Before acquisition, a line is parted on the subject's head in order to have an unobstructed view on the hair roots 11. As a consequence, pictures have an axial symmetry around their middle, and are thus generally oriented, with scalp 10 in the middle and more hairs in top and bottom.

The method is used to estimate an unbiased hair tone value h. However, this hair tone h is not directly readable from the acquired images I since they present a mix between hair 11 and scalp 10. Moreover, because of hair transparency the scalp color can influence the visible hair pixels.

Hence, the image I data shall be processed with the specific objective of obtaining accurate hair tones h. According to the present invention, the image data is processed by applying a machine learning model to said image before returning a numerical real-valued hair tone.

The machine learning models hereafter described have been statistically trained using a training set comprising 11175 pictures taken on 407 subjects. Each picture has been assessed and labelled with an actual value of the desired property (Training process is generally shown on FIG. 2).

Hair tone estimation has been done using the following two approaches namely a colorimetric model and a deep learning model based on a convolutional neural network (CNN).

Colorimetric Model

The idea behind this approach is to transform the imaging device into a colorimetric device that is able to provide standard color values of hair and relate them with the perceptual attribute of hair tone. The complete pipeline of this approach is separated in the three following steps shown on FIG. 3.

First, the acquired image I is pre-process through a segmentation step S. More precisely, the hair pixels of interest are segmented from the image. Then, the RGB values of the segmented hair pixels are transformed into CIELAB color space and a fitted colorimetric model M estimates the hair tone from the median L* value of hair. As such, this colorimetric approach involves the use of two independent machine learnings models successively applied to the image data: first a machine learning model is applied to perform the color space conversion, then a second machine learning model is applied for hair tone estimation form media hair L*.

Hair segmentation S is the first pre-processing step. The main objective of this step is to transform the different RGB values of hair pixels to a single integral L*a*b* value. Therefore, instead of segmenting all hair pixels in the image, which can introduce outliers, it is preferable to segment robustly an adequate number of hair pixels avoiding specularities and other artifacts. The segmentation method is based on adaptive thresholding in order to vastly segment hair form scalp areas. Before thresholding, a Gaussian filter is applied to reduce the noise in the image. Finally, the resulting hair regions are ranked by size using connected components analysis in order to eliminate small detected areas that could be specularities or other artifacts falsely segmented as hair.

Then the RGB values are converted to CIELab color space by applying machine learning model. More specifically, the camera device shall be calibrated in order to transform the device-dependent RGB values to a device-independent color space. The CIELAB color space was selected for this transformation since it is relatively perceptually uniform and is widely used in the industry.

There are various methods in the literature that provide L*a*b* measurements of hair. For the calibration process, it is proposed to estimate the L*a*b* value r∈ $\mathbb{R}^3$ of each RGB pixel expressed as x∈ $\mathbb{R}^3$, using the following model:

$$\hat{r}(x) = C_r \phi(x)$$

where $\phi(x)$ is a third degree polynomial (N=20) of the RGB pixel values x and $C_r$ are the corresponding coefficients, learned statistically by a machine learning model on a set of K training pairs. Those pairs were obtained by acquiring images of predefined color patches with measured L*a*b* values $r_i$. For each patch $x_i$ acquired by the device we take the median RGB pixels in order to solve the regression problem:

$$\underset{C_r}{\operatorname{argmin}} \sum_{i=1}^{K} \|\hat{r}(x_i) - r_i\|^2$$

which is the closed-form equation of $C_r$ and $\|0.1\|^2$ denotes the $L^2$ norm.

Once the hair pixels of interest are segmented, their RGB values are transformed into CIELAB space and the median L*a*b* values are kept. It has been noticed that the perceptual value that is most significantly varying between the different hair tones is lightness. In order to keep the model simple and avoid over-fitting on the data, the L* value is chosen as the most correlated value with the hair tone. Using the training set, a one-dimensional cubic smoothing spline $\hat{f}(l)$ is fit between the M pairs of L* and hair tone values, denoted as $l_i$ and $h_i$, respectively. These pairs of L* and hair tone values were computed by averaging on all the corresponding pictures of one participant. We automatically chose the number of the spline knots as the minimum number such that the following condition is met:

$$\frac{1}{M} \sum_{i=1}^{M} \|h(x_i) - \hat{f}(l_i)\|^2 \le \sigma^2$$

The smoothing factor $\sigma$ was set to 0.35, so as to ignore small variations along hair tone range [1; 10].

To conclude, the hair tone is predicted from a single input image I. We segment a subset of robust hair pixels x in I. Then, after converting each pixel x into L*a*b* space using $C_r\phi(x)$ we compute the median L* value l(I) of these pixels. Finally, the hair tone is given by applying machine learning model as:

$$\hat{h}(I) = \hat{f}(l(I))$$

Convolution Neural Network

The idea behind such an approach is to learn which patterns in the image are related to the hair tone, with no prior assumption on the patterns to extract. Contrary to the previous colorimetric model that is designed to focus on the lightness of hair pixels, this second one does not have prior knowledge of the problem. The optimization process is purely statistical and learns the patterns in an image I autonomously in order to estimate correct hair tone $\hat{h}(I)$.

The basic idea behind CNN is to apply successive linear operations, such as 3×3 convolutions, with non-linear functions in-between them as well as operations reducing the spatial dimension of the image representation. This produces feature maps of the image, which is a representation into visual patterns. After successive regressions, such representation is reduced to a single real-valued output, that will be eventually mapped to labels $h_i$ in the training process.

All these operations are represented as successive layers, shown in FIG. 4 for the network we propose for the present hair tone application. Compared to state-of-the-art CNN models, it has less convolutional layers; this is motivated by the fact that the we are looking for simpler patterns such as edges and thin fibers, requiring fewer successive convolutions to be represented by the network.

The final dense layers are also reduced, since we have a one dimensional output h(I). Moreover, residual connections were added to the architecture, in order to ease the optimization—direct links in back propagation—and extend model representation with simpler patterns.

For this purpose, we additioned the output of some layers to a latter layer, which is a light operation requiring no additional weights. In order to improve the speed, we use separable 2D convolutions, as a lighter alternative to regular 2D convolutions. They have less parameters to learn and require less computation. The idea is to first apply a 3×3 convolution channel by channel (also called depthwise), thus lighter than a full convolution, and then combine the resulting channels by a 1×1 full convolution. This variant of convolution will speed up the training process as well as the embedded prediction on device.

We now briefly explain the optimization process of such a model, in order to provide some intuition of how the neural network learns the relevant pattern for our problem. If we step back from the successive operations, we see that our estimated hair tone can be written as $$\hat{h}(I)=g(I,\Theta)$$

where g represents all successive operations of our neural network and $\Theta$ is a vector that regroups all the variable parameters, viz. convolutions and dense layers weights. In order to find appropriate values for $\Theta$, we define a loss function $\mathcal{L}(h(I),h)$ that penalizes predictions h(I) far from ground truth h. In our case, we minimize the mean square error $\mathcal{L}(h(I),h)=(\hat{h}(I)-h)^2$ over all images h and hair tones $h_i$ of our dataset:

$$\min_{\Theta} \sum_{i=1}^{M} \mathcal{L}(\hat{h}(I_i), h_i) = \min_{\Theta} \sum_{i=1}^{M} (g(I,\Theta) - h_i)^2$$

Our strategy to solve this minimization is to update iteratively $\Theta$ using stochastic gradient descent:

$$\Theta'=\Theta+\epsilon \widehat{\nabla_\Theta \mathcal{L}}$$

where $\epsilon$ is the learning rate and $\widehat{\nabla_\Theta \mathcal{L}}$ is an approximation of the gradient on the full data set. Indeed, this complete gradient $\Sigma_i \nabla_\Theta \mathcal{L}(\hat{h}(I_i),h_i)$ would be too long to compute for each update. Using back-propagation, the gradient can be computed efficiently for a minibatch of size m images. $\Theta$ is thus updated at each mini-batch by considering a moving average of the gradient $$\widehat{\nabla_\Theta \mathcal{L}}' = \lambda \widehat{\nabla_\Theta \mathcal{L}} + (1-\lambda)\frac{1}{m}\sum_{i \in B}\nabla_\Theta \mathcal{L}(\hat{h}(I_i), h_i)$$

where $\lambda$ is the momentum and B is the set of indices i of the mini-batch—$\mathcal{B} \subset \{1 \ldots M\}||\mathcal{B}|=m$.

Each mini-batch update of the weights is thus based on a history of the gradient and not only on the mini-batch gradient $\Sigma_{i \in B} \nabla_\Theta \mathcal{L}(\hat{h}(I_i),h_i)$, which presents high variations through mini-batches. In practice, we passed 800 times on all samples of our data set, with a learning rate of $\epsilon=10^{-4}$ and using a momentum of $\lambda=0:9$. At the end, in order to tune further the parameters $\Theta$, we passed 20 additional times on our data set with a learning rate divided by 10. During each pass, each image Ii is randomly flipped horizontally and vertically in order to augment artificially our data set. For our successive layers and the optimization process we used the implementation of Keras based on the Tensorflow backend.

Although illustrated by two machine learning models (colorimetric model & convolutional neural network model), other machine learning technics may be used, main aspect of the present application being the use of a statistical machine learning model in lieu of classical metrology using image analysis technique to directly extract the relevant parameter and actually performing a measurement.

The returned real-valued property may then be used as a parameter for further calculations or steps.

As a first possibility, the real-valued property may be used in a recommender, the method comprising a subsequent step of recommending a cosmetic product based on said real-valued characteristic.

As a second possibility, instead of recommending an existing product, the real-valued characteristic may be used to calculate or determine a composition of a cosmetic product based on a desired effect or result. More specifically, the method may comprise a step of calculation a proportion and/or amount of a component based on its alteration power of the rea-valued characteristic in order to achieve the desired result. For example, if a user wishes to dye its hair in order to reach a hair tone of 5 and its initial hair tone is 7, the method will comprise a step of calculating the amount of oxidant required to reach this result.

The determined composition may then be manufactured, on site or off site, and dispensed or delivered accordingly to the user.

As will be appreciated, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects. Furthermore, aspects of the present invention may take the form of a computer program product embodied in one or more computer readable medium(s) having computer readable program code embodied thereon.

Any combination of one or more computer readable medium(s) may be utilized. The computer readable medium may be, for example, but is not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a solid state disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a phase change memory storage device, or any suitable combination of the foregoing. In the context of this document, a computer readable storage medium may be any tangible medium that can contain, or store a program for use by or in connection with an instruction execution system, apparatus, or device.

Computer program code for carrying out operations for aspects of the present invention may be written in any combination of one or more programming languages, e.g., an object oriented programming language such as Java, Smalltalk, C++ or the like, or a conventional procedural programming language, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). It is to be understood that the software for the computer systems of the present invention embodiments may be developed by one of ordinary skill in the computer arts based on the functional descriptions contained in the specification and flow charts illustrated in the drawings. Further, any references herein of software performing various functions generally refer to computer systems or processors performing those functions under software control.

The various functions of the computer systems may be distributed in any manner among any quantity of software modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.).

More precisely, the above detailed method is implemented into a system for determining at least one physical and/or chemical characteristic of a keratinous surface of a user, said system comprising an image sensor configured for acquiring an image of the targeted keratinous surface, the image data being transmitted to a processor configured to process the image data according to the above described method, namely by applying the machine learning model and return a real-valued estimate of the characteristic. Such a system forms a diagnosis unit.

The system is integrated into a portable camera device. In a first embodiment, the camera device comprises the image sensor and the image data are processed outside the camera device in a distant processing unit. Advantageously, the image data are transmitted wirelessly. In an alternate embodiment, the system is fully integrated into the portable device, meaning that the camera device also comprises the processing unit. This way, the camera device can be used as an autonomous and/or real-time diagnosis unit directly outputting the real-valued property.

The system may comprise additional components in order to, for example, form a system for making a personalized cosmetic product, in particular a hair product, namely a hair coloring product. To this end, the system comprises a diagnosis unit as described above and a dispensing unit configured to deliver a cosmetic product according to characteristics obtained from the diagnosis unit. For a detailed description of a dispensing unit, one may refer to previously cited document U.S. Pat. No. 9,316,580 the content of which is hereby fully integrated.

The system and method described in the present application thus improves the overall automation of the personalization process. For hair treatment, in particular hair dying treatment, the automation of the process is vital in order to ease the life of hairdressers and equip them with tools that guarantee precision, robustness and efficiency. Moreover, using such devices we can go beyond the human visual perception and offer an objective notation that does not vary depending on the hairdresser and the conditions—in others terms, a standardized notation.

The foregoing examples are illustrative of certain functionality of embodiments of the invention and are not intended to be limiting. Indeed, other functionality and other possible use cases will be apparent to the skilled artisan upon review of this disclosure.

The invention claimed is:

1. A computer-implemented method for determining hair tone of a keratinous surface of a user, the method comprising the steps of:
   receiving data corresponding to at least one image of the keratinous surface encoded in a first color space, the at least one image picturing a scalp area of the user comprising hairs,
   performing a pre-processing segmentation step configured to identify at least one hair segment,
   processing the at least one image by transforming color values of the at least one identified hair segment from the first color space into a CIELAB color space including L* values by applying a first machine learning model to said at least one image,
   applying a second machine learning model trained accordingly to evaluate the hair tone of the keratinous surface from median L* values of pixels of the at least one identified hair segment, and
   returning at least one numerical value corresponding to a grade of the hair tone of the keratinous surface to be determined.

2. The computer-implemented method according to claim 1, wherein the segmentation step is performed by contrast analysis.

3. The computer-implemented method according to claim 1, wherein the segmentation step is performed by applying a classification model to the image.

4. The computer-implemented method according to claim 1, wherein the at least one image is an RGB image.

5. The computer-implemented method according to claim 1, wherein the method is repeated in order to determine a second characteristic of the keratinous surface.

6. The computer-implemented method according to claim 1, wherein the method comprises a subsequent step of recommending a cosmetic product based on the at least one numerical value.

7. The computer-implemented method according to claim 1, wherein the method comprises a subsequent step of determining a recommended cosmetic product composition based on the at least one numerical value.

8. The computer-implemented method according to claim 7, wherein the method comprises the subsequent step of making and dispensing a cosmetic product according to the recommended composition.

9. The computer-implemented method according to claim 1, wherein the area pictured in the at least one image is a hair-root region of the user.

10. The computer-implemented method according to claim 1, wherein the pre-processing segmentation step is based on adaptive thresholding by applying a Gaussian filter to reduce the noise in the image and then ranking hair regions by size using connected components analysis.

11. A non-transitory computer storage media storing computer-useable instructions that, when used by a computing device, cause the computing device to perform a method comprising:
   receiving data corresponding to at least one image of a keratinous surface of a user, the at least one image encoded in a first color space, the at least one image picturing a scalp area of the user comprising hairs, performing a pre-processing segmentation step configured to identify at least one hair segment, processing the at least one image by transforming color values of the at least one identified hair segment from the first color space into a CIELAB color space including L* values by applying a first machine learning model to the at least one image, applying a second machine learning model trained accordingly to evaluate hair tone of the keratinous surface from median L* values of pixels of the at least one identified hair segment, and returning at least one numerical value corresponding to a grade of the hair tone of the keratinous surface to be determined.

12. A system for determining hair tone of a keratinous surface of a user, said system comprising an image sensor configured for acquiring an image of the keratinous surface and to transmit the image data to a processor, said processor being configured to process the image data by performing steps comprising:

receiving data corresponding to at least one image of the keratinous surface encoded in a first color space, the at least one image picturing a scalp area of the user comprising hairs, performing a pre-processing segmentation step configured to identify at least one hair segment, processing the at least one image by transforming color values of the at least one identified hair segment from the first color space into a CIELAB color space including L* values by applying a first machine learning model to said at least one image, applying a second machine learning model trained accordingly to evaluate the hair tone of the keratinous surface from median L* values of pixels of the at least one identified hair segment, and returning at least one numerical value corresponding to a grade of the hair tone of the keratinous surface to be determined.

13. The system according to claim 12, wherein the system is at least partially integrated into a portable camera device.

14. The system according to claim 12, wherein the system comprises a camera device including the image sensor, said camera device being configured to transmit the image data wirelessly to a distant processing device.

15. The system according to claim 12 further comprising a dispensing unit configured to deliver a cosmetic product based on the at least one numerical value.

\* \* \* \* \*